(12) United States Patent
Godek et al.

(10) Patent No.: US 9,345,673 B2
(45) Date of Patent: May 24, 2016

(54) ANTI-CANCER CYCLOALKYL DIAMINES

(71) Applicants: Dennis Michael Godek, Glastonbury, CT (US); Harry Ralph Howard, Bristol, CT (US)

(72) Inventors: Dennis Michael Godek, Glastonbury, CT (US); Harry Ralph Howard, Bristol, CT (US)

(73) Assignee: MediSynergics, LLC, Newington, CT (US)

( * ) Notice: Subject to any disclaimer, the term of this patent is extended or adjusted under 35 U.S.C. 154(b) by 0 days.

(21) Appl. No.: 14/798,865

(22) Filed: Jul. 14, 2015

(65) Prior Publication Data

US 2016/0101068 A1    Apr. 14, 2016

Related U.S. Application Data

(63) Continuation-in-part of application No. 14/167,362, filed on Jan. 29, 2014, now Pat. No. 9,126,891.

(60) Provisional application No. 61/758,538, filed on Jan. 30, 2013.

(51) Int. Cl.

| | | |
|---|---|---|
| *A61K 31/428* | (2006.01) | |
| *A61K 31/426* | (2006.01) | |
| *A61K 31/135* | (2006.01) | |
| *A61K 31/4196* | (2006.01) | |
| *A61K 31/41* | (2006.01) | |
| *A61K 31/341* | (2006.01) | |
| *A61K 31/4409* | (2006.01) | |
| *A61K 31/4406* | (2006.01) | |
| *A61K 31/4164* | (2006.01) | |
| *A61K 31/40* | (2006.01) | |
| *A61K 31/5375* | (2006.01) | |
| *A61K 31/495* | (2006.01) | |
| *C07D 265/30* | (2006.01) | |
| *C07D 211/40* | (2006.01) | |
| *C07D 307/52* | (2006.01) | |
| *C07D 231/12* | (2006.01) | |
| *C07D 213/36* | (2006.01) | |

(52) U.S. Cl.
CPC ............. *A61K 31/135* (2013.01); *A61K 31/341* (2013.01); *A61K 31/40* (2013.01); *A61K 31/4164* (2013.01); *A61K 31/4406* (2013.01); *A61K 31/4409* (2013.01); *A61K 31/495* (2013.01); *A61K 31/5375* (2013.01)

(58) Field of Classification Search
CPC .. C07D 233/64; C07D 249/08; C07D 257/04; C07D 277/28; C07D 277/64; C07C 211/37; C07C 211/36; C07C 217/74; A61K 31/428; A61K 31/426; A61K 31/41; A61K 31/4196; A61K 31/417; A61K 31/131; A61K 31/138
See application file for complete search history.

(56) References Cited

U.S. PATENT DOCUMENTS

2009/0005456 A1 *   1/2009   Shao ................... C07C 215/42
                                                            514/650
2014/0221473 A1 *   8/2014   Amin .................. C07C 323/30
                                                            514/462

FOREIGN PATENT DOCUMENTS

CN            101308139 B  * 12/2012
WO      WO2006/048546 A1  *  5/2006

* cited by examiner

*Primary Examiner* — Nyeemah A. Grazier
*Assistant Examiner* — Amanda L Aguirre

(57) ABSTRACT

The invention is directed to a method of treatment of a cancer, in a mammal, the method comprising administering to said mammal in need of such treatment an effective amount of a cell growth inhibitory compound of formula I or a pharmaceutically acceptable salt form thereof.

5 Claims, No Drawings

ANTI-CANCER CYCLOALKYL DIAMINES

This application claims the benefit of U.S. Non-Provisional application Ser. No. 14/167,362 filed on Jan. 29, 2014.

BACKGROUND OF THE INVENTION

Cancer is a class of diseases characterized by out-of-control cell growth. There are more than 100 different types of cancer, and each is classified by the type of cell that is initially affected. A list of potential cancers that may be treated using one or more varieties of treatment (e.g., surgery, radiation, chemotherapy, immunotherapy, hormone therapy, gene therapy or combination therapies) includes cancer of bodily organs or tissues such as breast, prostate, kidney, brain, mouth, esophagus, stomach, intestine, colon, rectum, pancreas, bladder, uterus, cervix, ovary, vagina, testicle, liver and lung, as well as cancers of the circulatory system including leukemia and lymphoma, and skin cancers including basal cell and melanoma.

Cancer harms the body when altered cells divide uncontrollably to form tumors (except in the case of leukemia where cancer prohibits normal blood function by abnormal cell division in the blood stream). Tumors can grow and interfere with the digestive, nervous, and circulatory systems and they can release hormones that alter body function. Tumors that stay in one spot and demonstrate limited growth are generally considered to be benign. Malignant tumors form when one of the following occurs: a.) a cancerous cell manages to move throughout the body using the blood or lymphatic systems, destroying healthy tissue in a process called invasion, or b.) a cancerous cell begins to divide and grow, creating new blood vessels to feed itself in a process called angiogenesis. When a tumor successfully spreads to other parts of the body and grows, invading and destroying other healthy tissues, it is said to have metastasized and the condition becomes much more difficult to treat.

Cancer is considered to be one of the leading causes of morbidity and mortality worldwide. According to the American Cancer Society, cancer is the second most common cause of death in the US and accounts for nearly 1 of every 4 deaths. The World Health Organisation (WHO) estimates that, worldwide, there were 4 million new cancer cases and 8.2 million cancer-related deaths in 2012. In the US more than 575,000 people die of cancer, and more than 1.5 million people are diagnosed with cancer per year. According to WHO, the numbers of new cancer cases is expected to rise by about 70% over the next 20 years. The financial costs of cancer in the US per year are an estimated $263.8 billion in medical costs and lost productivity.

There continues to be an exceptionally high interest in developing safer and more efficacious anti-carcinoma drugs, in large part due to the growing awareness (e.g., early detection of breast and colon cancers) of the impact of cancer on patients and families, productivity and healthcare costs as portrayed in the media and through advocacy groups including the American Cancer society. Pharmaceutical and biotech companies continue to allocate significant resources to the discovery of effective, better tolerated and potentially more affordable treatments. In the ten-year period 2005-2014, the FDA approved a total of 84 new medications, with a high of 18 in 2012 (https://www.centerwatch.com/drug-information/fda-approved-drugs/therapeutic-area/12/oncology).

The present invention relates to the use of novel cycloalkyl-diamines and their pharmaceutical compositions for the treatment of cancer in mammals, including humans, and may provide a benefit with respect to efficacy or toleration in comparison to currently available chemo-therapeutic agents.

SUMMARY OF THE INVENTION

The present invention is directed to a method for the treatment of cancers in mammals, including humans, by administering a compound of the formula I, or a pharmaceutically effective salt(s) thereof, in an amount which is effective at inhibiting the growth of the cancer cells and carcinomas in said mammal, wherein:

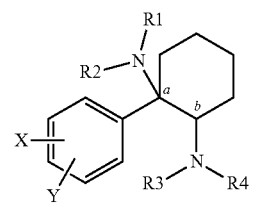

I

X and Y are independently selected from the group consisting of H, F, Cl, Br, I, CN, OH, $CF_3$, $C_2F_5$, $C_1$-$C_6$-alkyl, $C_3$-$C_7$-cycloalkyl, $C_1$-$C_3$-alkoxy, aryl, heteroaryl, —(C=O)—R5, —NH—(C=O)—R5, —NR5—(C=O)—R6, —(C=O)—NHR5 and —(C=O)—NR5R6;

R1 is hydrogen;
R2 is hydrogen or $C_1$-$C_6$-alkyl;
R3 is hydrogen or $C_1$-$C_6$-alkyl;
R4 is selected from the group consisting of $C_1$-$C_6$-alkyl, $C_3$-$C_7$-cycloalkyl, $(CH_2)_n$-R7, or
NR3R4 is a 5- to 12-membered cyclic or bicyclic ring system containing up to two additional heteroatoms in the ring, selected from N, O and S;
R5 is selected from $C_1$-$C_6$-alkyl and aryl;
R6 is selected from $C_1$-$C_6$-alkyl and aryl, or
NR5R6 is a 5- to 12-membered cyclic or bicyclic ring system containing up to two additional heteroatoms in the ring, selected from N, O and S;
R7 is independently selected from the group consisting of H, $C_1$-$C_6$-alkyl, $C_3$-$C_7$-cycloalkyl, ($C_1$-$C_6$-alkyloxy)-, ($C_1$-$C_6$-alkyloxy)-($C_1$-$C_6$-alkyl)-, NR8R9—, NR8R9—($C_1$-$C_6$-alkyl), aryl, heterocyclyl and heteroaryl;
R8 and R9 are independently selected from hydrogen, $C_1$-$C_6$-alkyl and aryl, or taken together with the N atom to which they are attached form a 3- to 8-membered ring containing up to two additional heteroatoms, selected from N, O and S; and
n is an integer between 0 and 6.

Preferred embodiments of the present invention include the compounds of formula I in which:
(A) R2 is methyl, R1 and R3 are hydrogen, Y is hydrogen;
  X is halogen;
  n is an integer between 0 to and 6; and
  R7 is aryl or heteroaryl.
(B) R2 is methyl, R1 and R3 are hydrogen; Y is hydrogen;
  X is halogen;
  n is an integer between 0 to and 6; and
  R7 is heterocyclyl.
(C) R2 is methyl; R1 and R3 are hydrogen; Y is hydrogen;
  X is halogen;
  n is an integer between 0 to and 6; and
  R7 is NR8R9.

Preferred compounds of formula I in accordance with the present invention include:

trans-1-(2-chlorophenyl)-$N^2$-(2-(dimethylamino)ethyl)-$N^1$-methylcyclohexane-1,2-diamine;

cis-1-(2-chlorophenyl)-$N^2$-(2-(dimethylamino)ethyl)-$N^1$-methylcyclohexane-1,2-diamine;

trans-1-(2-chlorophenyl)-$N^2$-cyclopropyl-$N^1$-methylcyclohexane-1,2-diamine;

cis-1-(2-chlorophenyl)-$N^2$-cyclopropyl-$N^1$-methylcyclohexane-1,2-diamine;

trans-1-(2-chlorophenyl)-$N^2$-cyclopentyl-$N^1$-methylcyclohexane-1,2-diamine;

cis-1-(2-chlorophenyl)-$N^2$-cyclopentyl-$N^1$-methylcyclohexane-1,2-diamine;

trans-1-(2-chlorophenyl)-$N^2$-(3-methoxypropyl)-$N^1$-methylcyclohexane-1,2-diamine;

cis-1-(2-chlorophenyl)-$N^2$-(3-methoxypropyl)-$N^1$-methylcyclohexane-1,2-diamine;

trans-1-(2-chlorophenyl)-$N^1$-methyl-$N^2$-(tetrahydrofuran-2-ylmethyl)cyclohexane-1,2-diamine;

cis-1-(2-chlorophenyl)-$N^1$-methyl-$N^2$-(tetrahydrofuran-2-ylmethyl)cyclohexane-1,2-diamine;

cis-1-(2-chloropheny)-$N^2$-(3-(dimethylamino)propyl)-$N^1$-methylcyclohexane-1,2-diamine;

trans-$N^2$-benzyl-1-(2-chlorophenyl)-$N^1$-methylcyclohexane-1,2-diamine;

cis-$N^2$-benzyl-1-(2-chlorophenyl)-$N^1$-methylcyclohexane-1,2-diamine;

cis-1-(2-chlorophenyl)-$N^1$-methyl-$N^2$-(pyridin-4-ylmethyl)cyclohexane-1,2-diamine;

trans-1-(2-chlorophenyl)-$N^1$-methyl-$N^2$-(pyridin-3-ylmethyl)cyclohexane-1,2-diamine;

cis-1-(2-chlorophenyl)-$N^2$-(1-(R)-phenyl)-ethyl)-$N^1$-methylcyclohexane-1,2-diamine;

trans-1-(2-chlorophenyl)-$N^2$-(1-(S)-phenyl)-ethyl)-$N^1$-methylcyclohexane-1,2-diamine;

trans-1-(2-chlorophenyl)-$N^2$-(3-(1-imidazolyl)-propyl)-$N^1$-methylcyclohexane-1,2-diamine;

cis-1-(2-chlorophenyl)-$N^2$-(3-(1-imidazolyl)-propyl)-$N^1$-methylcyclohexane-1,2-diamine;

trans-1-(2-chlorophenyl)-$N^2$-(1-ethyl-pyrrolidin-2-ylmethyl)-$N^1$-methylcyclohexane-1,2-diamine;

cis-1-(2-chlorophenyl)-$N^2$-(1-ethyl-pyrrolidin-2-ylmethyl)-$N^1$-methylcyclohexane-1,2-diamine;

trans-1-(2-chlorophenyl)-$N^2$-(3-(pyrrolidin-1-yl)propyl)-$N^1$-methylcyclohexane-1,2-diamine;

cis-1-(2-chlorophenyl)-$N^2$-(3-(pyrrolidin-1-yl)propyl)-$N^1$-methylcyclohexane-1,2-diamine;

trans-1-(2-chlorophenyl)-$N^2$-(3-phenylpropyl)-$N^1$-methylcyclohexane-1,2-diamine;

cis-1-(2-chlorophenyl)-$N^2$-(3-phenylpropyl)-$N^1$-methylcyclohexane-1,2-diamine;

trans-1-(2-chlorophenyl)-$N^2$-(3-(morpholin-1-yl)propyl)-$N^1$-methylcyclohexane-1,2-diamine;

cis-1-(2-chlorophenyl)-$N^2$-(3-(morpholin-1-yl)propyl)-$N^1$-methylcyclohexane-1,2-diamine;

trans-1-(2-chlorophenyl)-$N^2$-(3-(4-methylpiperazin-1-yl)propyl)-$N^1$-methylcyclohexane-1,2-diamine;

cis-1-(2-chlorophenyl)-$N^2$-(3-(4-methylpiperazin-1-yl)propyl)-$N^1$-methylcyclohexane-1,2-diamine;

trans-1-(2-chlorophenyl)-$N^2$-cyclohexyl-$N^1$-methylcyclohexane-1,2-diamine; and cis-1-(2-chlorophenyl)-$N^2$-cyclohexyl-$N^1$-methylcyclohexane-1,2-diamine.

Other compounds of the invention include the following:

1-(2-chloro-4-methoxyphenyl)-$N^2$-[3-(4,5-dimethyl-1H-imidazol-2-yl)propyl]-$N^1$-methyl-cyclohexane-1,2-diamine;

1-(2-chlorophenyl)-$N^1$-methyl-$N^2$-[3-(1H-1,2,4-triazol-5-yl)propyl]-cyclohexane-1,2-diamine;

1-(2-methylphenyl)-$N^1$-methyl-$N^2$-[3-(3-methyl-1H-1,2,4-triazol-5-yl)propyl]cyclohexane-1,2-diamine;

1-(2,4-dichlorophenyl)-$N^1$-methyl-$N^2$-[3-(1H-tetrazol-5-yl)propyl]-cyclohexane-1,2-diamine;

1-(3,4-fluorophenyl)-$N^1$-methyl-$N^2$-[2-(1-methyl-1H-tetrazol-5-yl)ethyl]-cyclohexane-1,2-diamine;

1-(4-chlorophenyl)-$N^2$-(2-(dimethylamino)ethyl)-$N^1$-methylcyclohexane-1,2-diamine;

1-(2,4-dichlorophenyl)-$N^2$-(2-(dimethylamino)ethyl)-$N^1$-methylcyclohexane-1,2-diamine;

1-(3,4-difluorophenyl)-$N^2$-(2-(dimethylamino)ethyl)-$N^1$-methylcyclohexane-1,2-diamine;

1-(4-isopropylphenyl)-$N^2$-(2-(dimethylamino)ethyl)-$N^1$-methylcyclohexane-1,2-diamine;

1-(2-methoxyphenyl)-$N^2$-(2-(dimethylamino)ethyl)-$N^1$-methylcyclohexane-1,2-diamine;

1-(2-chlorophenyl)-$N^2$-(2-(dimethylamino)ethyl)-$N^1$-methylcyclohexane-1,2-diamine;

1-(2-chlorophenyl)-$N^2$-[3-(1H-imidazol-2-yl)propyl]-$N^1$-methylcyclohexane-1,2-diamine;

1-(2-chlorophenyl)-$N^2$-[2-(1H-imidazol-2-yl)ethyl]-$N^1$-methylcyclohexane-1,2-diamine;

1-(2-chlorophenyl)-$N^1$-methyl-$N^2$-[3-(1,3-thiazol-2-yl)propyl]-cyclohexane-1,2-diamine;

1-(3,5-dimethyl-2-chlorophenyl)-$N^1$-methyl-$N^2$-[3-(1,3-thiazol-2-yl)propyl]-cyclohexane-1,2-diamine;

1-(3,5-dimethyl-phenyl)-$N^1$-methyl-$N^2$-[3-(4,5-dimethyl-1,3-thiazol-2-yl)propyl]-cyclohexane-1,2-diamine;

1-(2-chlorophenyl)-$N^2$-[3-(1,3-benzothiazol-2-yl)propyl]-$N^1$-methylcyclohexane-1,2-diamine;

1-(2,3-dichlorophenyl)-$N^2$-[3-(1,3-benzimidazol-2-yl)propyl]-$N^1$-methylcyclohexane-1,2-diamine;

1-(3,4-dichlorophenyl)-$N^2$-(2-(3,4-difluorophenypethyl)-$N^1$-methylcyclohexane-1,2-diamine;

1-(2-chlorophenyl)-$N^2$-(3-(3,4-difluorophenyl)propyl)-$N^1$-methylcyclohexane-1,2-diamine;

1-(2-chlorophenyl)-$N^2$-(3-(4-fluorophenyl)propyl)-$N^1$-methylcyclohexane-1,2-diamine;

1-(2-chlorophenyl)-$N^2$-(3-(3,4-dichlorophenyl)propyl)-$N^1$-methylcyclohexane-1,2-diamine;

1-(2-chlorophenyl)-$N^2$-(3-(4-methoxyphenyl)propyl)-$N^1$-methylcyclohexane-1,2-diamine;

1-(2-chlorophenyl)-$N^2$-[(4,5-dimethyl-1H-imidazol-2-yl)methyl]-$N^1$-ethylcyclohexane-1,2-diamine; and 1-(2-chlorophenyl)-$N^1$-ethyl-$N^2$-[(1-methyl-1H-imidazol-2-yl)methyl]cyclohexane-1,2-diamine.

DETAILED DESCRIPTION OF THE INVENTION

The compounds of formula I may be prepared as described in the following reaction schemes and discussions. Unless otherwise indicated, X, Y, R1, R2, R3, R4, R5, R6, R7 and structural formulae II, III, IV, V, VI, VII, VIII, IX, X, XI, XII, XIII, XIV and XV in the reaction schemes and discussion that follow are defined as above.

Scheme 1

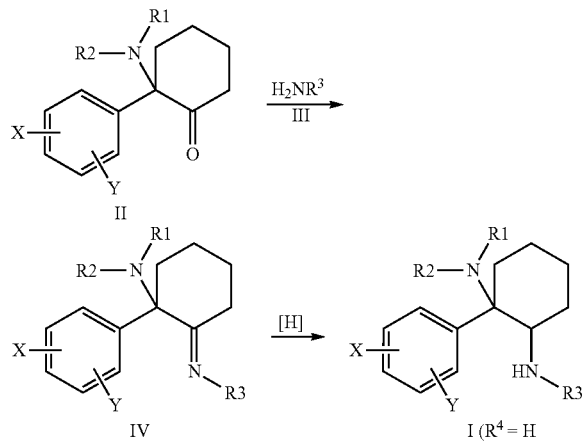

According to Scheme 1, a ketone of the general formula II, wherein X, Y, R$^1$ and R$^2$ are as previously defined, may be converted directly into the corresponding compound of the formula I, via an intermediate of the general formula IV, by reacting it with one or more equivalents of an primary amine of the general formula III in the presence of a reducing reagent. Reducing reagents that may be used include sodium cyanoborohydride, sodium triacetoxyborohydride, sodium borohydride, lithium aluminum hydride, hydrogen plus a metal catalyst, zinc plus hydrochloric acid, and formic acid. This reaction is typically conducted in a reaction inert solvent at a temperature from about 0° C. to about 150° C., but may be conducted in the absence of solvent. Suitable reaction inert solvents include lower alcohols (e.g., methanol, ethanol, isopropanol), 1,2-dichloroethane, acetic acid and tetrahydrofuran (THF)). Preferably the reaction is conducted with an excess of the corresponding amine III, in the absence of additional solvent, at a temperature of about 110° C., and using the reducing agent sodium cyanoborohydride.

Alternatively, the reaction of a compound of formula II with an amine compound of the formula III may be carried out in the presence of a dehydrating agent (e.g., titanium tetrachloride) or by using an apparatus designed to azeotropically remove the water generated, to produce an imine of the formula IV. This imine may then be converted to the title product of formula I by reduction of the C=N bond with a reducing agent as described above, preferably with sodium cyanoborohydride in the presence or absence of a suitable, reaction inert solvent as described in the preceding paragraph at a temperature of about 0° C. to about 150° C. and preferably at about 110° C. Other suitable dehydrating agents/solvent systems include titanium tetrachloride in dichloromethane, titanium isopropoxide in dichloromethane and activated molecular sieves in toluene or in dichloromethane.

Scheme 2

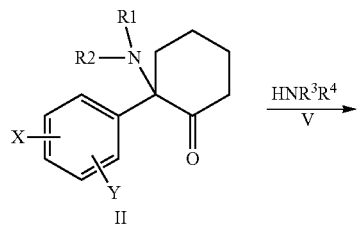

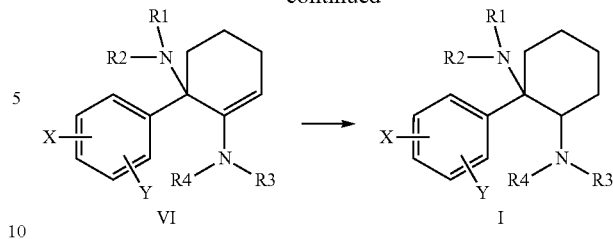

When a secondary amine of the general formula V (i.e., HNR3R4) is used, an alternative method involves the formation of an enamine of general formula VI, which can be reduced to the title product of formula I through the use of a selective reducing agent or selective reduction conditions known to one familiar with the art of organic synthesis. Using this procedure, as shown in Scheme 2 above, the intermediate enamine VI may be isolated and purified if it is stable, or it may be used directly in the reduction step to generate the diamine of general formula I. Selective reducing agents and reagents to facilitate the conversion of intermediate VI to the compounds of formula I include: formic acid, hydrogen gas and a metal catalyst (e.g., Pd on carbon, Pt on carbon).

In another method (Scheme 3) for the preparation of the compounds of the present invention, an intermediate oxime (VII) can be prepared through reaction of the starting ketone I and hydroxylamine. Synthesis of such oximes is well precedented in the chemical literature (e.g., see LaMattina J L, et al, *Synthesis* (1980) 329-330), and it is also known that intermediate oximes like VII are capable of forming two different isomers, denoted as Z- and E-oximes. These isomers Scheme 3

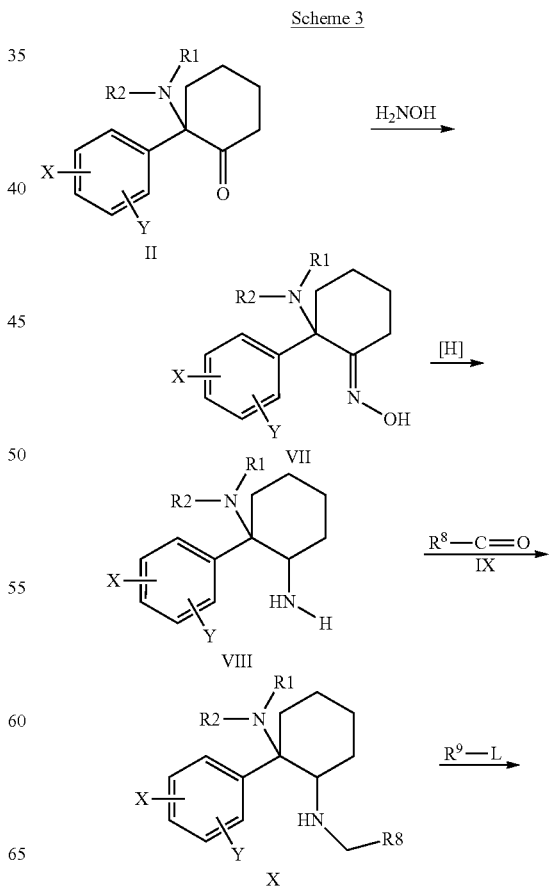

-continued

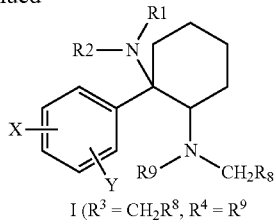

I (R³ = CH₂R⁸, R⁴ = R⁹)

may or may not react differently in their subsequent conversion to intermediates of general formulae VIII (i.e., I, R3, R4=H), and one of the oxime isomers may be less reactive or resistant to reduction to intermediate VIII. The reduction to VIII can be achieved using one of a variety of reagents and procedures, including Zn—AcOH, Na and $C_2H_5OH$, $BH_3$, and $NaBH_3CN$—$TiCl_3$.

In the next step, compound VIII can be converted to a compound of general formula X by subjecting it to a reductive amination with an aldehyde of general formula IX (for examples, see Jerry March, "Advanced Organic Chemistry: Reactions, Mechanisms and Structure",4[th] Ed., John Wiley & Sons, New York, N.Y. (1992) pp 898-900) followed by alkylation of the nitrogen atom of the intermediate of general formula X with a reagent of general formula R9-L, where L is a leaving group (e.g., Cl, Br, mesylate) and R9 is $C_1$-$C_3$ alkyl. Procedures for these reactions are readily available in the chemical literature and familiar to chemists with skill in the art of organic synthesis.

The starting ketone for the above processes, compound II, may be obtained from commercial sources or may be synthesized as described in the chemical literature (Scheme 4). Such compounds may exist as racemic mixtures or as the individual (+)- and (−)-isomers.

In general, 1-bromo-cyclopentane is converted to a Grignard reagent (XI) by reaction with magnesium metal in an inert solvent, typically in ethers like diethyl ether or tetrahydrofuran (THF). The Grignard reagent so formed is then reacted with an appropriately substituted arylnitrile (XII), in an inert solvent such as hexane, and stirred at room temperature until the reaction is determined to have been completed. The product, the arylketone (XIII), dissolved in a suitable solvent (e.g., chloroform) is then treated with one equivalent of bromine ($Br_2$), and the resulting α-bromo-ketone (XIV) is isolated by filtration. Compound XIV is then added to a primary amine of general formula R2—$NH_2$ in an inert solvent (e.g., toluene) and the mixture is heated to reflux. The Scheme 4

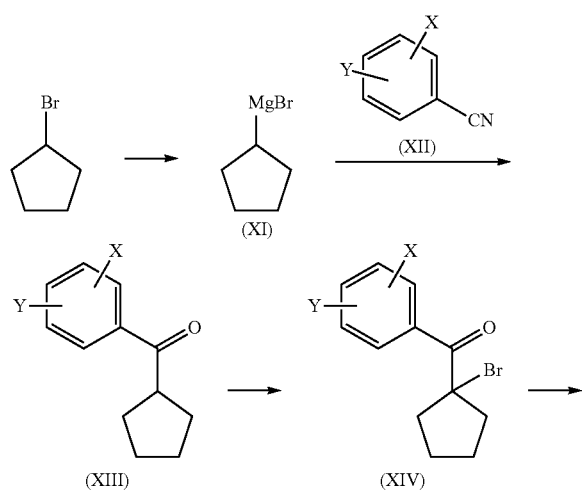

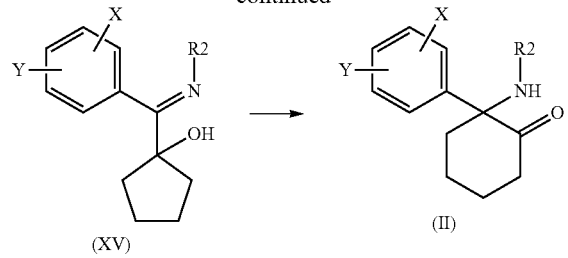

(XV) → (II)

solvents are subsequently removed under vacuum to obtain the crude α-hydroxy-imine (XV). This intermediate is then heated, typically in a high-boiling, inert solvent (e.g., decalin) wherein the compound undergoes a thermal rearrangement to produce the α-amino-ketone (II).

Specifically, the compound II in which X is 2-chloro, Y is H, R1 is hydrogen and R2 is methyl is commonly referred to as ketamine. Ketamine is a Central Nervous System active drug that may interact with NMDA (i.e., N-Methyl-D-Aspartate) receptors in the brain and has been associated with a variety of behavioral disorders in human and animal studies. The synthesis and utility of ketamine and related analogs as NMDA receptor modulators and disease treatments are described by T. G. Gant and S. Sarshar in US Patent Application 2008/109958 (Apr. 25, 2008).

The compounds of the present invention may have optical centers and therefore may occur in different enantiomeric configurations. Formula I, as depicted above, includes all enantiomers, diastereomers, and other stereoisomers of the compounds depicted in structural formula I, as well as racemic and other mixtures thereof. Individual isomers can be obtained by known methods, such as optical resolution, optically selective reaction, or chromatographic separation in the preparation of the final product or its intermediate.

Where cis- and trans-isomers are possible (i.e., at positions "a" and "b" in the structure of formula I), for an embodiment of the inventive compounds of formula I, both cis- and trans-isomers (i.e., diastereomers) are within the scope of this invention.

The present invention also includes isotopically labeled compounds, which are identical to those recited in formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, sulfur, phosphorus, fluorine, and chlorine, such as $^2H$, $^3H$, $^{11}C$, $^{13}C$, $^{13}N$, $^{15}N$, $^{18}O$, $^{35}S$, $^{31}P$, $^{33}P$, $^{18}F$ and $^{37}Cl$, respectively.

Compounds of the present invention, prodrugs thereof, and pharmaceutically acceptable salts of said compounds, or of said prodrugs which contain the aforementioned isotopes and/or other isotopes of other atoms are within the scope of this invention. Certain isotopically labeled compounds of the present invention, for example, those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of formula I of this invention and prodrugs thereof can generally be prepared by carrying out the procedures disclosed in the Schemes and/or in the Examples and Preparations below, by substituting a readily available isotopically labeled reagent for a non-isotopically labeled reagent.

The term "alkyl" refers to straight or branched chains of carbon atoms. Exemplary alkyl groups are $C_3$-$C_{10}$ alkyl groups which include methyl, ethyl, propyl, isopropyl, butyl, isobutyl, pentyl, isopentyl, hexyl and the like, including all regioisomeric forms thereof, and straight and branched chain forms thereof. The term "alkyl" is also used to denote straight or branched chains of carbon atoms having one or more carbon-carbon double bonds, such as vinyl, allyl, butenyl and the like, as well as straight and branched chains of carbon atoms having one or more carbon-carbon triple bonds, such as ethynyl, propargyl, butynyl, and the like.

The term "aryl" denotes a cyclic, aromatic hydrocarbon. Examples include phenyl, naphthyl, anthracenyl, phenanthracenyl, and the like.

The terms "alkoxy" and "aryloxy" denote "O-alkyl" and "O-aryl", respectively. The term "cycloalkyl" denotes a cyclic group of carbon atoms, where the ring formed by the carbon atoms may be saturated or may comprise one or more carbon double bonds in the ring. Examples of cycloalkyl groups include cyclopropyl, cyclobutyl, cyclopentyl, cyclohexyl, cycloheptyl, and the like as well as cyclopentenyl, cyclopentadienyl, cyclohexenyl, cyclohexadienyl, and the like. As used herein, the term "cycloalkyl" is also intended to denote a cyclic group comprising at least two fused rings, such as adamantyl, decahydronaphthalinyl, norbornanyl, where the cyclic group may also have one or more carbon-carbon double bonds in one or more rings, such as in bicyclo (4.3.0)nona-3,6(1)-dienyl, dicyclopentadienyl, 1,2,3,4-tetrahydro-naphthalinyl (i.e., tetralinyl), indenyl, and the like.

The term "halogen" represents chloro, fluoro, bromo and iodo.

The term "heteroaryl" denotes a monocyclic or bicyclic aromatic group wherein one or more carbon atoms are replaced with heteroatoms selected from the group consisting of nitrogen, oxygen, and sulfur. If the heteroaryl group contains more than one heteroatom, the heteroatoms may be the same or different. Preferred heteroaryl groups are five- to fourteen-member rings that contain from one to three heteroatoms independently selected from oxygen, nitrogen, and sulfur. Examples of preferred heteroaryl groups include, but are not limited to, benzo[b]thienyl, chromenyl, furyl, imidazolyl, indazolyl, indolizinyl, indolyl, isobenzofuranyl, isoindolyl, isoquinolinyl, isothiazolyl, isoxazolyl, napthylidinyl, oxadiazolyl, oxazinyl, oxazolyl, phthalazinyl, pteridinyl, purinyl, pyranyl, pyrazinyl, pyrazolyl, pyridazinyl, pyridinyl, triazolyl, tetrazolyl and the like.

A "unit dosage form" as used herein is any form that contains a unit dose of the compound of formula I. A unit dosage form may be, for example, in the form of a tablet or a capsule. The unit dosage form may also be in liquid form, such as a solution or suspension.

The compositions of the present invention may be formulated in a conventional manner using one or more pharmaceutically acceptable carriers. Thus, the active compounds of the present invention may be formulated for oral, buckle, intranasal, parenteral (e.g., intravenous, intramuscular or subcutaneous) or rectal administration or in a form suitable for administration by inhalation or insufflations.

For oral administration, the pharmaceutical compositions may take the form of, for example, tablets or capsules prepared by conventional means with pharmaceutically acceptable excipients such as binding agents (e.g., pre-gelatinized maize starch, polyvinylpyrrolidone or hydroxypropyl methylcellulose), fillers (e.g., lactose, microcrystalline cellulose or calcium phosphate); lubricants (e.g., magnesium stearate, talc, or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating agents such as suspending, stabilizing and/or dispensing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichloro-fluoromethane, dichlorotetrachloroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insulator may be formulated containing a powder mix of a compound of the invention and a suitable powder base such as lactose or starch.

A proposed dose of the active compounds of the invention for oral, parenteral or buccal administration to the average adult human for the treatment of the conditions referred to above is from about 0.1 mg/kg to about 100 mg/kg of the active ingredient per unit dose which could be administered, for example, one to four times per day. Toxicity concerns at the higher level may restrict intravenous (i.v.) dosages to a lower level, such as up to 10 mg/kg. A dose of about 0.1 mg/kg to about 100 mg/kg may be employed for oral (p.o.) administration. Typically, a dosage from about 0.1 mg/kg to about 10 mg/kg may be employed for intramuscular (i.m.) injection. Preferred dosages are in the 1.0 mg/kg to about 100 mg/kg range, and more preferably in the 5 mg/kg to about 50 mg/kg range for i.v. or p.o. administration. The duration of the treatment is usually once per day for a period of one days to three weeks, or until the condition is essentially brought under control.

Aerosol formulations for treatment of the conditions referred to above in the average human are preferably arranged such that each metered dose or "puff" of aerosol contains 0.1 micrograms to 100 micrograms of the active compound of the invention. The overall daily dose with an aerosol will be within the range of 0.1 mg/kg to about 100 mg/kg, and preferably in the range of 1.0 mg/kg to about 25 mg/kg. Administration may be several times daily, for example 2, 3, 4 or 8 times, giving for example 1, 2 or 3 doses each time.

As an example, the mammal in need of treatment or prevention may be a human. As another example, the mammal in need of treatment or prevention may be a mammal other than a human.

A compound of formula I which is basic in nature is capable of forming a wide variety of different salts with various inorganic and organic acids. The acid additions salts are readily prepared by treating the base compounds with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid salts of the active compound used in formulating the pharmaceutical composition of this invention that are basic in nature are those which form non-toxic acid addition salts, e.g., salts containing pharmacologically acceptable anions. Non-limiting examples of the salts include the acetate, benzoate, beta-hydroxybutyrate, bisulfate, bisulfite, bromide, butyne-1,4-dioate, caproate, chloride, chlorobenzoate, citrate, dihydrogen phosphate, dinitrobenzoate, fumarate, glycollate, heptanoate, hexyne-1,6-dioate, hydroxybenzoate, iodide, lactate, maleate, malonate, mandelate, metaphosphate, methanesulfonate, methoxybenzoate, monohydrogen phosphate, naphthalene-1-sulfonate, naphthalene-2-sulfonate, oxalate, phenyl butyrate, phenylpropionate, phosphate, phthalate, phenylacetate, propanesulfonate, propiolate, propionate, pyrophosphate, pyrosulfate, sebacate, suberate, succinate, sulfate, sulfite, sulfonate, tartrate, xylenesulfonate, acid phosphate, acid citrate, bitartrate, succinate, gluconate, saccharate, nitrate, methanesulfonate, and pamoate {i.e., 1,1'-methylene-bis-(2-hydroxy-3-naphthoate)} salts.

Also included within the scope of this invention are solvates and hydrates of compounds of formula I and their pharmaceutically acceptable salts. The present invention includes within its scope all possible stoichiometric and non-stoichiometric forms.

In the examples that follow, the abbreviations used in this document are intended to have the following, general meaning:
bm: broad multiplet (NMR)
bs: broad singlet (NMR)
d: doublet (NMR)
dd: doublet of doublets (NMR)
d.e.: diatomaceous earth, filtering agent
calcd.: calculated value
J: coupling constant (NMR)
LC: high pressure liquid chromatography (HPLC)
m: multiplet (NMR)
min: minute(s)
m/z: mass to charge ratio (mass spectroscopy)
obsd: observed value
Rf: retention factor (chromatography)
RT: retention time (chromatography)
rt: room temperature (typically 25° C.)
s: singlet (NMR)
t: triplet (NMR),
T: temperature
tlc: thin layer chromatography
TFA: trifluoroacetic acid
THF: tetrahydrofuran Solvents were purchased and used without purification. Yields were calculated for material judged to be homogeneous by thin layer chromatography and NMR. Thin layer chromatography was performed on Kieselgel plates eluting with the indicated solvents, visualized by using a 254 nm UV lamp, and stained with either an aqueous $KMnO_4$ solution or an ethanolic solution of 12-molybdophosphoric acid.

Nuclear Magnetic Resonance (NMR) spectra were acquired on a 400 MHz NMR Spectrometer. Chemical shifts for proton $^1H$-NMR spectra are reported in parts per million (ppm) relative to the singlet of $CDCl_3$ at 7.24 ppm.
Preparative Conditions for Chromatographic Purification and Analysis.
Instrument: LaChrom HPLC system (Merck-Hitachi) for UV-directed purification and Waters HPLC/MS for mass directed purification, both equipped with RP $C_{18}$ column (Phenomenex Gemini NX 5μ 150mm×30mm).
Eluent I:
  A: Acetonitrile-$H_2O$=5:95, 10 mM $NH_4HCO_3$ buffer, pH 8.0
  B: Acetonitrile-$H_2O$=80:20 10 mM $NH_4HCO_3$ buffer, pH 8.0
Eluent II:
  A: Acetonitrile-$H_2O$=5:95, 20 mM $HCOONH_4/NH_4OH$ buffer, pH 7.4
  B: Acetonitrile-$H_2O$=80:20, 20 mM $HCOONH_4/NH_4OH$ buffer, pH 7.4
Eluent III:
  A: Acetonitrile-$H_2O$=5:95, 20 mM $CH_3COONH_4/CH_3COOH$ buffer, pH 6
  B: Acetonitrile-$H_2O$=80:20, 20 mM $CH_3COONH_4/CH_3COOH$ buffer, pH 6
Eluent IV:
  A: $H_2O$ with 0.1% TFA, pH 2.2
  B: Acetonitrile with 0.1% TFA, pH 2.2
Gradient program: adjusted according to the compound properties
Column Temp.: room temperature (25° C.)
Flow Rate: up to 40 ml/min
Detection and triggering: UV detector (220 nm)
Conditions for LC-MS Analysis:
Column: Zorbax RRHD Eclipse XDB (Agilent) $C_{18}$, 1.9 micron, 50 mm×2.1 mm.
Eluent I:
  A: Acetonitrile-$H_2O$=5:95, 20 mM $HCOONH_4/NH_4OH$ buffer, pH 7.4
  B: Acetonitrile-$H_2O$=80:20, 20 mM $HCOONH_4/NH_4OH$ buffer, pH 7.4
Eluent I:
  A: $H_2O$ with 0.1% TFA, pH 2.2
  B: Acetonitrile with 0.1% TFA, pH 2.2
Gradient program: adjusted according to the compound properties; typically, start: 0% B to 100% B in 1 minute, 0.8 minute isocratic B.
Column Temp.: 40° C.
Flow Rate: 0.6 mL/min
Sample Conc.: ca. 1 mg/mL
Sample Solvent: Acetonitrile
Injection: 0.5 μL
Detection wavelength: 220 nm
  MS conditions:
Measured Mass Range: 100-750 Daltons
Scan Time: 0.2 s
Ion mode: ES±

Cone Voltage: 20 V
Capillary Voltage: 3 V
Source temp.: 140° C.
Desolvation temp.: 450° C.
Desolvation gas: 450 L/h
Cone gas: 60 L/h

EXAMPLE 1

General Procedure A

Trans-1-(2-chlorophenyl)-$N^2$-(2-(dimethylamino) ethyl)-$N^1$-methylcyclohexane-1,2-diamine (1a) and Cis-1-(2-chlorophenyl)-$N^2$-(2-(dimethylamino) ethyl)-$N^1$-methylcyclohexane-1,2-diamine (1b)

A mixture of 2-(2-chlorophenyl)-2-(methylamino)cyclohexanone hydrochloride (ketamine HCl) (423 mg, 1.54 mmol) and $N^1,N^1$-dimethylethane-1,2-diamine (1.6 mL, 19.2 mmol) was heated at 110° C. for 20 h. The mixture was cooled to room temperature and sodium cyano-borohydride (490 mg, 7.8 mmol) was added. The mixture was then heated at 110° C. overnight. The cooled reaction mixture was quenched with saturated $NaHCO_3$, extracted with $CH_2Cl_2$ (75 mL), dried ($Na_2SO_4$) and concentrated to dryness to give 500 mg of crude product (M/Z 310 [$M^+$+H]). This material was further purified by column chromatography, as described in Method A above.

a.) The product fractions, (RT=0.50) were combined, the solvents were removed and the trans-isomer was isolated as a trifluoroacetate salt, 0.149 g.

MS: calcd. for $C_{17}H_{28}ClN_3$: 309.9; obsd.: 309.2 (m+1).

$^1$H-nmr (DMSO-$d_6$, 400 MHz, T=30° C.) δ 1.4-1.7 (m, 3H), 1.75-2.0 (m, 3H), 2.10-2.35 (m+s, 5H), 2.40-2.50 (m+s, 6H), 2.75-2.85 (m, 2H), 2.92 (m, 1H), 3.15 (m, 1H), 7.40-7.50 (m, 2H), 7.55-7.65 (m, 2H), 8.5 (bs, 1H).

b.) The more polar fractions (RT=0.64) were separately combined and, after removal of the solvents, the cis-isomer was isolated as a solid, 0.078 g.

MS: calcd. for $C_{17}H_{28}ClN_3$: 309.9; obsd.: 309.19 (m+1).

The following compounds were also prepared using the general procedure A, as described above for the title compounds of Examples 1:

EXAMPLE 2

Trans-1-(2-chlorophenyl)-$N^2$-cyclopropylmethyl-$N^1$-methylcyclohexane-1, 2-diamine (2a), and Cis-1-(2-chlorophenyl)-$N^2$-cyclopropylmethyl-$N^1$-methylcyclohexane-1,2-diamine (2b)

The title compounds of Example 2 were prepared according to general procedure A using cyclopropylmethanamine and ketamine.

a.) LC (RT=0.55)/Mass spectrum (m/z) calcd. for $C_{17}H_{25}ClN_2$: 292.8; obsd.: 293 (M+1, 100%), 295 (M+1, 37Cl, 30%), 262 (28%).

$^1$H-nmr (DMSO-$d_6$, 400 MHz, T=30° C.) δ 0.1 (m, 2H), 0.2 (m, 2H), 0.5 (m, 2H), 0.85 (m, 1H), 1.50 (m, 2H), 1.65 (d, 1H), 1.85-2.10 (m, 2H), 2.05 (s, 3H), 2.15 (m, 2H), 2.30-2.55 (m, 2H), 2.70 (dd, 1H), 4.45 (s, 1H), 7.40-7.65 (m, 4H).

b.) LC (RT=0.72)/MS: calcd. for $C_{17}H_{25}ClN_2$: 292.8; obsd.: 293 (M+1).

$^1$H-nmr (DMSO-d6, 400 MHz, T=30° C.) δ 0.30 (m, 2H), 0.55 (dd, 2H), 1.0 (m, 1H), 1.2 (m, 1H), 1.40-1.85 (m, 5H), 2.05 (m+s, 4H), 2.80 (m, 3H), 4.20 (m, 1H), 6.5 (bs, 2H), 7.35-7.50 (m, 2H), 7.52 (dd, 1H), 7.64 (d, 1H).

EXAMPLE 3

Trans-1-(2-chlorophenyl)-$N^2$-cyclopentyl-$N^1$-methylcyclohexane-1,2-diamine (3a), and Cis-1-(2-chlorophenyl)-$N^2$-cyclopentyl-$N^1$-methylcyclohexane-1, 2-diamine (3b)

The title compounds of Example 3 were prepared according to general procedure A using cyclopentylamine and ketamine.

a.) LC (RT=0.58)/MS: calcd. for $C_{18}H_{27}ClN_2$: 306.9; obsd.: 306.19 (m+1).

b.) LC (RT=0.96)/MS: calcd. for $C_{18}H_{27}ClN_2$: 306.9; obsd.: 306.19 (m+1).

EXAMPLE 4

Trans-1-(2-chlorophenyl)-$N^2$-(3-methoxypropyl)-$N^1$-methylcyclohexane-1,2-diamine (4a), and Cis-1-(2-chlorophenyl)-$N^2$-(3-methoxypropyl)-$N^1$-methylcyclohexane-1,2-diamine (4b)

The title compounds of Example 4 were prepared according to general procedure A using 3-methoxypropylamine and ketamine.

a.) LC (RT=0.59)/MS: calcd. for $C_{17}H_{27}ClN_2O$: 310.9; obsd.: 310.18 (m+1).

b.) LC (RT=0.67)/MS: calcd. for $C_{17}H_{27}ClN_2O$: 310.9; obsd.: 310.18 (m+1).

EXAMPLE 5

Trans-1-(2-chlorophenyl)-$N^1$-methyl-$N^2$-(tetrahydrofuran-2-ylmethyl)cyclohexane-1,2-diamine (5a), and Cis-1-(2-chlorophenyl)-$N^1$-methyl-$N^2$-(tetrahydrofuran-2-ylmethyl)cyclohexane-1,2-diamine (5b)

The title compounds of Example 5 were prepared according to general procedure A using 2-aminomethyl-2,3,4,5-tetrahydrofuran and ketamine.

a.) LC (RT=0.63)/MS: calcd. for $C_{18}H_{27}ClN_2O$: 322.9; obsd.: 322.18 (m+1).

b.) LC (RT=0.70)/MS: calcd. for $C_{18}H_{27}ClN_2O$: 322.9; obsd.: 322.18 (m+1).

EXAMPLE 6

Cis-1-(2-chloropheny)-$N^2$-(3-(dimethylamino)propyl) $N^1$-methyl-cyclohexane-1,2-diamine (6)

The title compound of Example 6 was prepared according to general procedure A using 3-(N,N-dimethylamino)-propylamine and ketamine.

LC (RT=0.66)/MS: calcd. for $C_{18}H_{30}ClN_3$: 323.9; obsd.: 323.21 (m+1).

EXAMPLE 7

Trans-$N^2$-benzyl-1-(2-chlorophenyl)-$N^1$-methylcyclohexane-1,2-diamine (7a) and Cis-$N^2$-benzyl-1-(2-chlorophenyl)-$N^1$-methylcyclohexane-1,2-diamine (7b)

The title compounds of Example 7 were prepared according to general procedure A using benzylamine and ketamine.

a.) LC (RT=0.66)/MS: calcd. for $C_{20}H_{25}ClN_2$: 328.9; obsd.: 328.17 (m+1).
b.) LC (RT=1.01)/MS: calcd. for $C_{20}H_{25}ClN_2$: 328.9; obsd.: 328.17 (m+1).

EXAMPLE 8

Cis-1-(2-chlorophenyl)-$N^1$-methyl-$N^2$-(pyridin-4-ylmethyl)cyclohexane-1,2-diamine (8)

The title compound of Example 8 was prepared according to general procedure A using 4-(aminomethyl)-pyridine and ketamine.
LC (RT=0.70)/MS: calcd. for $C_{19}H_{24}ClN_3$: 329.9; obsd.: 329.17 (m+1).

EXAMPLE 9

Trans-1-(2-chlorophenyl)-$N^1$-methyl-$N^2$-(pyridin-3-ylmethyl)cyclohexane-1,2-diamine (9)

The title compound of Example 9 was prepared according to general procedure A using 3-(aminomethyl)-pyridine and ketamine.
LC (RT=0.56)/MS: calcd. for $C_{19}H_{23}ClN_3$: 329.9; obsd.: 329.17 (m+1).

EXAMPLE 10

Cis-1-(2-chlorophenyl)-$N^2$-(1-(R)-phenyl)-ethyl)-$N^1$-methylcyclohexane-1,2-diamine (10)

The title compound of Example 10 was prepared according to general procedure A using (R)-α-methyl-benzylamine and ketamine.
LC (RT=1.05)/MS: calcd. for $C_{21}H_{27}ClN_2$: 342.9; obsd.: 342.19 (m+1).

EXAMPLE 11

Trans-1-(2-chlorophenyl)-$N^2$-(1-(S)-phenyl)-ethyl)-$N^1$-methylcyclohexane-1,2-diamine (11)

The title compound of Example 11 was prepared according to general procedure A using (S)-α-methyl-benzylamine and ketamine.
LC (RT=0.81)/MS: calcd. for $C_{21}H_{27}ClN_2$: 342.9; obsd.: 342.19 (m+1).

EXAMPLE 12

Trans-1-(2-chlorophenyl)-$N^2$-(3-(1-imidazolyl)-propyl)-$N^1$-methylcyclohexane-1,2-diamine (12a), and Cis-1-(2-chlorophenyl)-$N^2$-(3-(1-imidazolyl)-propyl)-$N^1$-methylcyclohexane-1,2-diamine (12b)

The title compounds of Example 12 were prepared according to general procedure A using 3-(1-imidazolyl)-propylamine and ketamine.
a.) LC (RT=0.70)/MS: calcd. for $C_{19}H_{27}ClN_4$: 346.9; obsd.: 346.19 (m+1).
$^1$H-nmr (DMSO-d6, 400 MHz, T=30° C.) δ 1.35-1.55 (m, 2H), 1.60-1.75 (m, 1H), 1.80-2.00 (m, 4H), 2.05-2.35 (m+s, 6H), 2.45-2.70 (m, 2H), 3.95-4.25 (m, 3H), 7.40-7.50 (m, 3H), 7.55 (m, 1H), 7.60 (m, 1H), 7.70 (s, 1H), 8.95 (s, 1H).
b.) LC (RT=0.54)/MS: calcd. for $C_{19}H_{27}ClN_4$: 346.9; obsd.: 346.19 (m+1).
$^1$H-nmr (DMSO-d6, 400 MHz, T=30° C.) δ 1.25 (bs, 1H), 1.40 (bs, 1H), 1.50-1.80 (m, 4H), 1.90 (m, 1H), 2.00-2.25 (m+s, 5H), 2.55 (m, 1H), 2.70-2.95 (m, 2H), 3.90 (bs, 1H), 4.20-4.35 (m, 2H), 6.50 (bs, 2H), 7.40-7.45 (m, 2H), 7.52 (m, 1H), 7.65 (m, 1H), 7.70 (m, 1H), 7.75 (m, 1H), 9.10 (s, 1H).

EXAMPLE 13

Trans-1-(2-chlorophenyl)-$N^2$-(1-ethyl-pyrrolidin-2-ylmethyl)-$N^1$-methylcyclohexane-1,2-diamine (13a), and Cis-1-(2-chlorophenyl)-$N^2$-(1-ethyl-pyrrolidin-2-ylmethyl)-$N^1$-methylcyclohexane-1,2-diamine (13b)

The title compounds of Example 13 were prepared according to general procedure A using N-ethyl-2-(aminomethyl)-pyrrolidine and ketamine.
a.) LC (RT=0.55)/MS: calcd. for $C_{20}H_{32}ClN_3$: 349.9; obsd.: 349.23 (m+1).
b.) LC (RT=0.70)/MS: calcd. for $C_{20}H_{32}ClN_3$: 349.9; obsd.: 349.23 (m+1).

EXAMPLE 14

Trans-1-(2-chlorophenyl)-$N^2$-(3-(pyrrolidin-1-yl)propyl)-$N^1$-methylcyclohexane-1,2-diamine (14a), and Cis-1-(2-chlorophenyl)-$N^2$-(3-(pyrrolidin-1-yl)propyl)-$N^1$-methylcyclohexane-1,2-diamine (14b)

The title compounds of Example 14 were prepared according to general procedure A using N-(3-aminopropyl)-pyrrolidine and ketamine.
a.) LC (RT=0.50)/MS: calcd. for $C_{20}H_{32}ClN_3$: 349.9; obsd.: 349.23 (m+1).
b.) LC (RT=0.68)/MS: calcd. for $C_{20}H_{32}ClN_3$: 349.9; obsd.: 349.23 (m+1).

EXAMPLE 15

Trans-1-(2-chlorophenyl)-$N^2$-(3-phenylpropyl)-$N^1$-methylcyclohexane-1,2-diamine (15a), and Cis-1-(2-chlorophenyl)-$N^2$-(3-phenylpropyl)-$N^1$-methylcyclohexane-1,2-diamine (15b)

The title compounds of Example 15 were prepared according to general procedure A using 3-aminopropylbenzene and ketamine.
a.) LC (RT=0.71)/MS: calcd. for $C_{22}H_{29}ClN_2$: 356.9; obsd.: 356.19 (m+1).
b.) LC (RT=0.77)/MS: calcd. for $C_{22}H_{29}ClN_2$: 356.9; obsd.: 356.19 (m+1).

EXAMPLE 16

Trans-1-(2-chlorophenyl)-$N^2$-(3-(morpholin-1-yl)propyl)-$N^1$-methylcyclohexane-1,2-diamine (16a), and Cis-1-(2-chlorophenyl)-$N^2$-(3-(morpholin-1-yl)propyl)-$N^1$-methylcyclohexane-1,2-diamine (16b)

The title compounds of Example 16 were prepared according to general procedure A using N-(3-aminopropyl)-morpholine and ketamine.
a.) LC (RT=0.49)/MS: calcd. for $C_{20}H_{32}ClN_3O$: 365.9; obsd.: 365.22 (m+1).
b.) LC (RT=0.86)/MS: calcd. for $C_{20}H_{32}ClN_3O$: 365.9; obsd.: 365.22 (m+1).

EXAMPLE 17

Trans-1-(2-chlorophenyl)-N²-(3-(4-methylpiperazin-1-yl)propyl)-N¹-methylcyclohexane-1,2-diamine (17a), and Cis-1-(2-chlorophenyl)-N²-(3-(4-methylpiperazin-1-yl)propyl)-N¹-methylcyclohexane-1,2-diamine (17b)

The title compounds of Example 17 were prepared according to general procedure A using N¹-methyl-N²-(3-aminopropyl)-piperazine and ketamine.
    a.) LC (RT=0.48)/MS: calcd. for $C_{21}H_{35}ClN_4$: 378.9; obsd.: 378.26 (m+1).
    b.) LC (RT=0.69)/MS: calcd. for $C_{21}H_{35}ClN_4$: 378.9; obsd.: 378.26 (m+1).

EXAMPLE 18

Trans-1-(2-chlorophenyl)-N²-cyclohexyl-N¹-methylcyclohexane-1,2-diamine (18a), and Cis-1-(2-chlorophenyl)-N²-cyclohexyl-N¹-methylcyclohexane-1,2-diamine (18b)

The title compounds of Example 18 were prepared according to general procedure A using cyclohexylamine and ketamine.
    a.) LC (RT=1.55)/MS: calcd. for $C_{19}H_{29}ClN_2$: 320.9; obsd.: 320.19 (m+1).
    b.) LC (RT=1.05)/MS: calcd. for $C_{19}H_{29}ClN_2$: 320.9; obsd.: 320.19 (m+1).

EXAMPLE 19

General Procedure B

Cis-(1R,2R)-1-(2-chlorophenyl)-N²-(3-phenylpropyl)-N¹-methylcyclohexane-1,2-diamine (19a), and Cis-(1S,2S)-1-(2-chlorophenyl)-N²-(3-phenylpropyl)-N¹-methylcyclohexane-1,2-diamine (19b)

The title compound of Example 15b (110 mg) was purified using high pressure liquid chromatography (HPLC) under the following conditions:
Instrument: JASCO-SFC (SuperCritical Fluid Chromatography) Semi-Prep HPLC (JASCO Inc., Easton, Md., USA).
Stationary Phase: Diacel Chiralpak AS-H, 10 mm column.
Mobile Phase: Ethanol/CO₂. Isocratic 5% EtOH/95% CO₂.
Detection: UV detection at 220, 254 nM.
Column Temp.: 25° C.
Flow Rate: 2.5 mL/min
    Fraction 1 (19a): 35 mg. RT=7.187 min, ee>99%, purity >98%.
    Fraction 2 (19b): 30 mg. RT=8.347 min, ee>99%, purity >95%. Mass Spectrum: (ESI⁺ scan) 357.2 $(M_{35Cl}+H)^+$, 359 $(M_{37Cl}+H)^+$.

EXAMPLE 20

Cis-(1R,2R)-1-(2-chlorophenyl)-N²-(3-(morpholin-1-yl)propyl)-N¹-methylcyclohexane-1,2-diamine (20a), and Cis-(1S,2S)-1-(2-chlorophenyl)-N²-(3-(morpholin-1-yl)propyl)-N¹-methylcyclohexane-1,2-diamine (20b)

The title compound of Example 16b (60 mg) was purified using high pressure liquid chromatography (HPLC) under the conditions described in Example 19 above.
    Fraction 1 (20a): 17 mg. RT=10.192 min, ee>99%, purity >99%.
Mass Spec (ESI+, Acquisition Time=2.546 min): m/z=366.23 (100%, (M+H)⁺), 368 (33%, (M+H)⁺ for Cl³⁷).

Fraction 2 (20b): 18 mg. RT=12.783 min, ee>99%, purity >99%.
Mass Spec (ESI+, Acquisition Time=2.548 min): m/z=366.23 (100%, (M+H)⁺), 368 (33%, (M+H)⁺ for Cl³⁷).

Determination of Biological Activity

Methodology of the In Vitro Cancer Screen

The human tumor cell lines of the cancer screening panel are grown in RPMI 1640 medium containing 5% fetal bovine serum and 2 mM L-glutamine. For a typical screening experiment, cells are inoculated into 96 well microtiter plates in 100 µL at plating densities ranging from 5,000 to 40,000 cells/well depending on the doubling time of individual cell lines. After cell inoculation, the microtiter plates are incubated at 37° C., 5% CO₂, 95% air and 100% relative humidity for 24 h prior to addition of experimental drugs. After 24 h, two plates of each cell line are fixed in situ with TCA, to represent a measurement of the cell population for each cell line at the time of drug addition (Tz). Experimental drugs are solubilized in dimethyl sulfoxide at 400-fold the desired final maximum test concentration and stored frozen prior to use. At the time of drug addition, an aliquot of frozen concentrate is thawed and diluted to twice the desired final maximum test concentration with complete medium containing 50 µg/ml gentamicin. Additional four, 10-fold or ½ log serial dilutions are made to provide a total of five drug concentrations plus control. Aliquots of 100 µl of these different drug dilutions are added to the appropriate microtiter wells already containing 100 µl of medium, resulting in the required final drug concentrations.

Following drug addition, the plates are incubated for an additional 48 h at 37° C., 5% CO₂, 95% air, and 100% relative humidity. For adherent cells, the assay is terminated by the addition of cold TCA. Cells are fixed in situ by the gentle addition of 50 µl of cold 50% (w/v) TCA (final concentration, 10% TCA) and incubated for 60 minutes at 4° C. The supernatant is discarded, and the plates are washed five times with tap water and air dried. Sulforhodamine B (SRB) solution (100 µl) at 0.4% (w/v) in 1% acetic acid is added to each well, and plates are incubated for 10 minutes at room temperature. After staining, unbound dye is removed by washing five times with 1% acetic acid and the plates are air dried. Bound stain is subsequently solubilized with 10 mM trizma base, and the absorbance is read on an automated plate reader at a wavelength of 515 nm. For suspension cells, the methodology is the same except that the assay is terminated by fixing settled cells at the bottom of the wells by gently adding 50 µl of 80% TCA (final concentration, 16% TCA). Using the seven absorbance measurements [time zero, (Tz), control growth, (C), and test growth in the presence of drug at the five concentration levels (Ti)], the percentage growth is calculated at each of the drug concentrations levels. Percentage growth inhibition is calculated as:

[(Ti−Tz)/(C−Tz)]×100 for concentrations for which Ti>/=Tz
[(Ti−Tz)/Tz]×100 for concentrations for which Ti<Tz.

Three dose response parameters are calculated for each experimental agent. Growth inhibition of 50% (GI50) is calculated from [(Ti−Tz)/(C−Tz)]×100=50, which is the drug concentration resulting in a 50% reduction in the net protein increase (as measured by SRB staining) in control cells during the drug incubation. The drug concentration resulting in total growth inhibition (TGI) is calculated from Ti=Tz. The LC50 (concentration of drug resulting in a 50% reduction in the measured protein at the end of the drug treatment as compared to that at the beginning) indicating a net loss of cells following treatment is calculated from [(Ti−Tz)/Tz]×100=−50. Values are calculated for each of these three parameters if the level of activity is reached; however, if the effect is not reached or is exceeded, the value for that parameter is expressed as greater or less than the maximum or minimum concentration tested.

REFERENCES

Alley, M C, Scudiero, D A, Monks, P A, Hursey, M L, Czerwinski, M J, Fine, D L, Abbott, B J, Mayo, J G, Shoemaker, R H, and Boyd, M R. Feasibility of Drug Screening with Panels of Human Tumor Cell Lines Using a Microculture Tetrazolium Assay. Cancer Research 48: 589-601, 1988.

Grever, M R, Schepartz, S A, and Chabner, B A. The National Cancer Institute: Cancer Drug Discovery and Development Program. Seminars in Oncology, Vol. 19, No. 6, pp 622-638, 1992.

Boyd, M R and Paull, K D. Some Practical Considerations and Applications of the National Cancer Institute In Vitro Anticancer Drug Discovery Screen. Drug Development Research 34: 91-109, 1995.

Review: Shoemaker, R H. The NCI60 Human Tumour Cell line Anticancer Drug Screen. Nature Reviews, 6: 813-823, 2006.

Data
Cell Line, Mean Growth Percent (%) at 10 μM

| | Leukemia | | | Non-SCLC* HOP-92 | Renal | | Prostate | Breast MDA-MB- |
| --- | --- | --- | --- | --- | --- | --- | --- | --- |
| Example | K-562 | Molt-4 | RPMI-8226 | | A-498 | UO-31 | PC-3 | 231/ATCC |
| 12b | 98.6 | 105 | 100 | 79.1 | 73.3 | 82.5 | 89.2 | 75.5 |
| 13a | 98.4 | 102.8 | 106.5 | 87.5 | 71.5 | 65.0 | 87.0 | 89.3 |
| 13b | 79.7 | 95.9 | 102 | 77.8 | 74.7 | 70.9 | 90.9 | 72.0 |
| 15b | 30.8 | 72.5 | 61.0 | 61.6 | 75.5 | 76.1 | 73.3 | 74.0 |
| 16b | 100 | 112 | 87.8 | 85.0 | 73.9 | 82.2 | 84.4 | 83.1 |
| 17b | 85.6 | 97.5 | 86.6 | 82.5 | 86.1 | 64.4 | 81.9 | n.d. | n.d. - not determined
*Non-small cell lung cancer

The invention claimed is:

1. A method of inhibiting cell growth in cancer cells, wherein the cancer is leukemia, non-small cell lung cancer, renal cancer, prostate cancer or breast cancer, comprising administering to a mammal in need of said treatment an effective amount of a cell growth inhibitory compound of the formula (I):

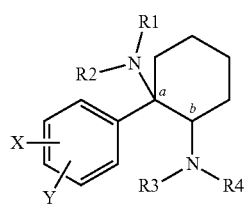

(I)

or the pharmaceutically acceptable salt thereof, wherein:
X and Y are independently selected from the group consisting of H, F, Cl, Br, I, CN, OH, $CF_3$, $C_2F_5$, $C_1$-$C_6$-alkyl, $C_3$-$C_7$-cycloalkyl, $C_1$-$C_3$-alkoxy, aryl, heteroaryl, —(—C=O)—R5, —NH—(C=O)—R5, —NR5—(C=O)—R6, —(C=O)—NHR5 and —(C=O)—NR5R6
R1 is hydrogen;
R2 is hydrogen or $C_1$-$C_6$-alkyl;
R3 is hydrogen or $C_1$-$C_6$-alkyl;
R4 is selected from the group consisting of $C_1$-$C_6$-alkyl, $C_3$-$C_7$-cycloalkyl and $(CH_2)_n$—R7, or
NR3R4 is a 5- to 12-membered cyclic or bicyclic ring system containing up to two additional heteroatoms in the ring, selected from N, O and S;
R5 is selected from $C_1$-$C_6$-alkyl and aryl;
R6 is selected from $C_1$-$C_6$-alkyl and aryl, or
NR5R6 is a 5- to 12-membered cyclic or bicyclic ring system containing up to two additional heteroatoms in the ring, selected from N, O and S;
R7 is independently selected from the group consisting of H, $C_1$-$C_6$-alkyl, $C_3$-$C_7$-cycloalkyl, ($C_1$-$C_6$-alkyloxy)-, $C_1$-$C_6$-alkyloxy)-$C_1$-$C_6$-alkyl)-, NR8R9—, NR8R9—($C_1$-$C_6$-alkyl), aryl, heterocyclyl and heteroaryl; and
R8 and R9 are independently selected from hydrogen, $C_1$-$C_6$-alkyl and aryl, or taken together with the N atom to which they are attached form a 3- to 8-membered ring containing up to two additional heteroatoms, selected from N, O and S; and
n is an integer between 0 and 6.

2. The method of claim 1 wherein R4 is $C_1$-$C_6$-alkyl, $C_3$-$C_7$-cycloalkyl or $(CH_2)_n$—R7 and wherein n is an integer between 0 and 6.

3. The method of claim 1 wherein R7 is selected from the group consisting of H, $C_1$-$C_6$-alkyl, $C_3$-$C_7$-cycloalkyl, ($C_1$-$C_6$-alkyloxy)-($C_1$-$C_6$-alkyl)-, NR8R9—($C_1$-$C_6$-alkyl)-, aryl, heterocyclyl and heteroaryl.

4. The method of claim 1 wherein said compound is selected from:
trans-1-(2-chlorophenyl)-$N^2$-(2-(dimethylamino)ethyl)-$N^1$-methylcyclohexane-1,2-diamine;
cis-1-(2-chlorophenyl)-$N^2$-(2-(dimethylamino)ethyl)-$N^1$-methylcyclohexane-1,2-diamine;
trans-1-(2-chlorophenyl)-$N^2$-cyclopropyl-$N^1$-methylcyclohexane-1,2-diamine;
cis-1-(2-chlorophenyl)-$N^2$-cyclopropyl-$N^1$-methylcyclohexane-1,2-diamine;
trans-1-(2-chlorophenyl)-$N^2$-cyclopentyl-$N^1$-methylcyclohexane-1,2-diamine;
cis-1-(2-chlorophenyl)-$N^2$-cyclopentyl-$N^1$-methylcyclohexane-1,2-diamine;
trans-1-(2-chlorophenyl)-$N^2$-(3-methoxypropyl)-$N^1$-methylcyclohexane-1,2-diamine;
cis-1-(2-chlorophenyl)-$N^2$-(3-methoxypropyl)-$N^1$-methylcyclohexane-1,2-diamine;
trans-1-(2-chlorophenyl)-$N^1$-methyl-$N^2$-(tetrahydrofuran-2-ylmethyl)cyclohexane-1,2-diamine;
cis-1-(2-chlorophenyl)-$N^1$-methyl-$N^2$-(tetrahydrofuran-2-ylmethyl)cyclohexane-1,2-diamine;
cis-1-(2-chloropheny)-$N^2$-(3-(dimethylamino)propyl)-$N^1$-methylcyclohexane-1,2-diamine;

trans-N²-benzyl-1-(2-chlorophenyl)-N¹-methylcyclohexane-1,2-diamine;
cis-N²-benzyl-1-(2-chlorophenyl)-N¹-methylcyclohexane-1,2-diamine;
cis-1-(2-chlorophenyl)-N¹-methyl-N²-(pyridin-4-ylmethyl)cyclohexane-1,2-diamine;
trans-1-(2-chlorophenyl)-N¹-methyl-N²-(pyridin-3-ylmethyl)cyclohexane-1,2-diamine;
cis-(2-chlorophenyl)-N²-(1-(R)-phenyl)-ethyl)-N¹-methylcyclohexane-1,2-diamine;
trans-(2-chlorophenyl)-N²-(1-(S)-phenyl)-ethyl)-N¹-methylcyclohexane-1,2-diamine;
trans-(2-chlorophenyl)-N²-(3-(1-imidazolyl)-propyl)-N¹-methylcyclohexane-1,2-diamine;
cis-(2-chlorophenyl)-N²-(3-(1-imidazolyl)-propyl)-N¹-methylcyclohexane-1,2-diamine;
trans-(2-chlorophenyl)-N²-(1-ethyl-pyrrolidin-2-ylmethyl)-N¹-methylcyclohexane-1,2-diamine;
cis-(2-chlorophenyl)-N²-(1-ethyl-pyrrolidin-2-ylmethyl)-N¹-methylcyclohexane-1,2-diamine;
trans-(2-chlorophenyl)-N²-(3-(pyrrolidin-1-yl)propyl)-N¹-methylcyclohexane-1,2-diamine;
cis-(2-chlorophenyl)-N²-(3-(pyrrolidin-1-yl)propyl)-N¹-methylcyclohexane-1,2-diamine;
trans-1-(2-chlorophenyl)-N²-(3-phenylpropyl)-N¹-methylcyclohexane-1,2-diamine;
cis-(2-chlorophenyl)-N²-(3-phenylpropyl)-N¹-methylcyclohexane-1,2-diamine;
trans-1-(2-chlorophenyl)-N²-(3-(morpholin-1-yl)propyl)-N¹-methylcyclohexane-1,2-diamine;
cis-1-(2-chlorophenyl)-N²-(3-(morpholin-1-yl)propyl)-N¹-methylcyclohexane-1,2-diamine;
trans-1-(2-chlorophenyl)-N²-(3-(4-methylpiperazin-1-yl)propyl)-N¹-methylcyclohexane-1,2-diamine;
cis-1-(2-chlorophenyl)-N²-(3-(4-methylpiperazin-1-yl)propyl)-N¹-methylcyclohexane-1,2-diamine;
trans-1-(2-chlorophenyl)-N²-cyclohexyl-N¹-methylcyclohexane-1,2-diamine; and
cis-1-(2-chlorophenyl)-N²-(2-(dimethylamino)ethyl)-N¹-methylcyclohexane-1,2-diamine.

5. The method of claim 1 wherein the compound is selected from the group consisting of:
1-(2-chloro-4-methoxyphenyl)-N²-[3-(4,5-dimethyl-1H-imidazol-2-yl)propyl]-N¹-methyl-cyclohexane-1,2-diamine;
1-(2-chlorophenyl)-N¹-methyl-N²-[3-(1H-1,2,4-triazol-5-yl)propyl]-cyclohexane-1,2-diamine;
1-(2-methylphenyl)-N¹-methyl-N²-[3-(3-methyl-1H-1,2,4-triazol-5-yl)propyl]-cyclohexane-1,2-diamine;
1-(2,4-dichlorophenyl)-N¹-methyl-N²-[3-(1H-tetrazol-5-yl)propyl]-cyclohexane-1,2-diamine;
1-(3,4-fluorophenyl)-N¹-methyl-N²-[2-(1-methyl-1H-tetrazol-5-yl)ethyl]-cyclohexane-1,2-diamine;
1-(4-chlorophenyl)-N²-(2-(dimethylamino)ethyl)-N¹-methylcyclohexane-1,2-diamine;
1-(2,4-dichlorophenyl)-N²-(2-(dimethylamino)ethyl)-N¹-methylcyclohexane-1,2-diamine;
1-(3,4-difluorophenyl)-N²-(2-(dimethylamino)ethyl)-N¹-methylcyclohexane-1,2-diamine;
1-(4-isopropylphenyl)-N²-(2-(dimethylamino)ethyl)-N¹-methylcyclohexane-1,2-diamine;
1-(2-methoxyphenyl)-N²-(2-(dimethylamino)ethyl)-N¹-methylcyclohexane-1,2-diamine;
1-(2-chlorophenyl)-N²-(2-(dimethylamino)ethyl)-N¹-methylcyclohexane-1,2-diamine;
1-(2-chlorophenyl)-N²-[3-(1H-imidazol-2-yl)propyl]-N¹-methylcyclohexane-1,2-diamine;
1-(2-chlorophenyl)-N²-[2-(1H-imidazol-2-yl)ethyl]-N¹-methylcyclohexane-1,2-diamine;
1-(2-chlorophenyl)-N¹-methyl-N²-[3-(1,3-thiazol-2-yl)propyl]-cyclohexane-1,2-diamine;
1-(3,5-dimethyl-2-chlorophenyl)-N¹-methyl-N²-[3-(1,3-thiazol-2-yl)propyl]-cyclohexane-1,2-diamine;
1-(3,5-dimethyl-phenyl)-N¹-methyl-N²-[3-(4,5-dimethyl-1,3-thiazol-2-yl)propyl]-cyclohexane-1,2-diamine;
1-(2-chlorophenyl)-N²-[3-(1,3-benzothiazol-2-yl)propyl]-N¹-methylcyclohexane-1,2-diamine;
1-(2,3-dichlorophenyl)-N²-[3-(1,3-benzimidazol-2-yl)propyl]-N¹-methylcyclohexane-1,2-diamine;
1-(3,4-dichlorophenyl)-N²-(2-(3,4-difluorophenyl)ethyl)-N¹-methylcyclohexane-1,2-diamine;
1-(2-chlorophenyl)-N²-(3-(3,4-difluorophenyl)propyl)-N¹-methylcyclohexane-1,2-diamine;
1-(2-chlorophenyl)-N²-(3-(4-fluorophenyl)propyl)-N¹-methylcyclohexane-1,2-diamine;
1-(2-chlorophenyl)-N²-(3-(3,4-dichlorophenyl)propyl)-N¹-methylcyclohexane-1,2-diamine;
1-(2-chlorophenyl)-N²-(3-(4-methoxyphenyl)propyl)-N¹-methylcyclohexane-1,2-diamine;
1-(2-chlorophenyl)-N²-[(4,5-dimethyl-1H-imidazol-2-yl)methyl]-N¹-ethylcyclohexane-1,2-diamine; and
1-(2-chlorophenyl)-N¹-ethyl-N²-[(1-methyl-1H-imidazol-2-yl)methyl]cyclohexane-1,2-diamine.

* * * * *